US006267984B1

(12) United States Patent
Beste et al.

(10) Patent No.: US 6,267,984 B1
(45) Date of Patent: Jul. 31, 2001

(54) SKIN PERMEATION ENHANCER COMPOSITIONS COMPRISING A MONOGLYCERIDE AND ETHYL PALMITATE

(75) Inventors: Russell D. Beste, Mountain View; Richard D. Hamlin, Newark, both of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/213,835

(22) Filed: Dec. 17, 1998

Related U.S. Application Data
(60) Provisional application No. 60/068,411, filed on Dec. 22, 1997.

(51) Int. Cl.[7] .............................. A61K 9/70; A61K 9/14; A61F 13/00
(52) U.S. Cl. ...................... 424/449; 424/447; 424/448; 424/484; 424/485; 424/486; 424/487; 424/488
(58) Field of Search .................................. 424/448, 449, 424/447, 484, 485, 486, 487, 488

(56) References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | Smith | 424/21 |
| 4,144,317 | 3/1979 | Higuchi | 424/361 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,999 | 3/1986 | Netto | 623/7 |
| 4,645,502 | 2/1987 | Gale et al. | 604/896 |
| 4,704,282 | 11/1987 | Campbell et al. | 424/449 |
| 4,746,515 | 5/1988 | Cheng et al. | 424/449 |
| 4,751,087 | 6/1988 | Wick | 424/449 |
| 4,764,379 | 8/1988 | Sanders et al. | 424/449 |
| 4,788,062 | 11/1988 | Gale et al. | 424/449 |
| 4,816,258 | 3/1989 | Nedberge et al. | 424/448 |
| 4,820,720 | 4/1989 | Sanders et al. | 514/356 |
| 4,849,226 | 7/1989 | Gale | 424/448 |
| 4,863,738 | 9/1989 | Taskovich | 424/449 |
| 4,863,970 | 9/1989 | Patel et al. | 514/784 |
| 4,865,848 | 9/1989 | Cheng et al. | 424/449 |
| 4,900,555 | 2/1990 | Cheng et al. | 424/449 |
| 4,908,027 | 3/1990 | Enscore et al. | 604/890.1 |
| 4,940,586 | 7/1990 | Cheng et al. | 424/464 |
| 4,943,435 | 7/1990 | Baker et al. | 424/448 |
| 4,973,468 | 11/1990 | Chiang et al. | 424/449 |
| 5,004,610 | 4/1991 | Osborne et al. | 424/448 |
| 5,006,342 | 4/1991 | Cleary et al. | 424/445 |
| 5,026,556 | 6/1991 | Drust et al. | 424/449 |
| 5,053,227 | 10/1991 | Chiang et al. | 424/448 |
| 5,059,426 | 10/1991 | Chiang et al. | 424/449 |
| 5,122,382 | 6/1992 | Gale et al. | 424/449 |
| 5,149,538 | 9/1992 | Granger et al. | 424/449 |
| 5,176,916 | 1/1993 | Yamanaka et al. | 424/448 |
| 5,314,694 | 5/1994 | Gale et al. | 424/448 |
| 5,352,456 | 10/1994 | Fallon et al. | 424/448 |
| 5,378,730 | 1/1995 | Lee et al. | 514/535 |
| 5,411,740 | 5/1995 | Lee et al. | 424/448 |
| 5,629,019 | 5/1997 | Lee et al. | 424/489 |
| 5,641,504 | 6/1997 | Lee et al. | 424/447 |
| 5,650,165 | 7/1997 | Akemi et al. | 424/448 |
| 5,686,097 | 11/1997 | Taskovich et al. | 424/448 |
| B1 3,598,122 | 11/1982 | Zaffaroni | 128/268 |
| B1 4,588,580 | 1/1989 | Gale et al. | 424/21 |

FOREIGN PATENT DOCUMENTS

| | | | |
|---|---|---|---|
| 573 133 A1 | 10/1989 | (EP) | A61K/31/565 |
| 1011949 | 12/1965 | (GB) . | |
| WO95/01167 | 1/1995 | (WO) | A61K/9/70 |
| WO95/09006 | 4/1995 | (WO) | A61K/47/14 |
| 96/37231 | 11/1996 | (WO) | A61K/47/14 |
| WO96/40259 | 12/1996 | (WO) | A61K/47/14 |

OTHER PUBLICATIONS

Williams et al. "Skin Absorption Enhancers" *Critical Review in Therapeutic Drug Carrier Systems*, pp. 305–353 (1992).

Santus et al. "Transdermal Enhancer Patent Literature", *Journal of Controlled Release*, pp. 1–20 (1993).

*Primary Examiner*—Shelley A. Dodson
(74) *Attorney, Agent, or Firm*—Vandana Date; Steven Stone

(57) ABSTRACT

Compositions, devices, and methods for transdermal administration of a drug are disclosed using a novel permeation enhancer mixture comprising a monoglyceride and ethyl palmitate. The monoglyceride/ethyl palmitate permeation enhancer is a potent permeation enhancer and provides stable systems which are more readily characterized. Additionally, ethyl palmitate cosolvent systems are more readily processed at manufacturing conditions thus providing further advantages over other cosolvents.

36 Claims, 2 Drawing Sheets

SKIN PERMEATION ENHANCER COMPOSITIONS COMPRISING A MONOGLYCERIDE AND ETHYL PALMITATE

RELATED APPLICATION

This application claims the benefit of U.S. Provisional Application No. 60/068,411, filed on Dec. 22, 1997.

TECHNICAL FIELD

This invention relates to the transdermal delivery of drugs and more particularly to methods and compositions for enhancing the percutaneous absorption of drugs when incorporated in transdermal drug delivery systems or devices. More particularly and without limitation, this invention relates to the transdermal delivery of drugs utilizing a novel permeation enhancer comprising a monoglyceride, preferably glycerol monolaurate, and ethyl palmitate as a cosolvent.

BACKGROUND ART

The transdermal route of parenteral delivery of drugs provides many advantages, and transdermal systems for delivering a wide variety of drugs are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,943,435; 5,004,610; 5,006,342; 5,314,694; 5,411,740; 5,629,019; 5,641,504; 5,686,097 for example, all of which are incorporated herein by reference. In many cases, drugs which would appear to be ideal candidates for transdermal delivery are found to have such low permeability through intact skin that they cannot be delivered in therapeutically effective amounts from reasonably sized devices.

In an effort to increase skin permeability so that drugs can be delivered in therapeutically effective amounts, it has been proposed to pretreat the skin with various chemicals or to concurrently deliver the drug in the presence of a permeation enhancer. Various materials have been suggested for this, as described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,568,343; 4,746,515; 4,764,379; 4,788,062; 4,820,720; 4,863,738; 4,863,970; 4,865,848; 4,900,555; 4,940,586; 4,973,468; 5,053,227; 5,059,426; 5,378,730; and WO 95/01167, all of which are hereby incorporated in their entirety by reference. Williams et al. "Skin Absorption Enhancers" *Critical Review in Therapeutic Drug Carrier Systems*, pp. 305–353 (1992) and Santus et al. "Transdermal Enhancer Patent Literature", *Journal of Controlled Release*, pp. 1–20 (1993) also provide a recent review of transdermal permeation enhancers.

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–60 cm$^2$) is at therapeutically effective levels. Additionally, the permeation enhancer when applied to the skin surface, should be non-toxic, non-irritating on prolonged exposure and under occlusion, and non-sensitizing on repeated exposure. Preferably, it should be odorless, physiologically inactive, and capable of delivering drugs without producing burning or tingling sensations.

In addition to these permeation enhancer-skin interaction considerations, a permeation enhancer must also be evaluated with respect to possible interactions within the transdermal system itself. For example, the permeation enhancer must be compatible with the drug to be delivered, the adhesive, and the polymer matrix in which the drug is dispersed. The permeation enhancer should also be selected so as to ensure a suitable balance among tack, adhesion, and cohesive strength of the adhesive.

The use of a cosolvent in combination with a permeation enhancer has also been disclosed in the prior art. Such cosolverits may not appreciably increase transdermal flux by themselves, but act synergistically to increase the transdermal flux of a drug when used in combination with other permeation enhancers such as monoglycerides. One theory is that these cosolvents act to increase the availability of the permeation enhancer at the skin surface, thus providing increased flux of drug.

For example, U.S., WO 95/09006 discloses the use of various lactic acid ester cosolvents such as lauryl lactate, ethyl lactate, cetyl lactate, and myristyl lactate in combination with a monoglyceride. However, these lactic acid esters may be irritating to the skin. Further, these lactate esters are not commercially available at a high degree of purity, thus causing regulatory concerns as they are not readily characterized.

WO 96/40259 discloses the use of lauryl acetate as a cosolvent for monoglyceride permeation enhancers such as GML. This combination provides enhanced flux when compared to other monoglyceride/cosolvent combinations and is available at a high degree of purity.

However, lauryl acetate has been found to be an undesirable cosolvent from a manufacturing standpoint. For example, it has been found that an undesirable amount of lauryl acetate evaporates during manufacturing of transdermal systems due to its high vapor pressure, leaving insufficient amounts of lauryl acetate in the system.

Therefore, in spite of these advances, problems associated with skin irritation and more recently discovered problems associated with processing and manufacturing of films comprising various cosolvents for monoglycerides have left a need for improved monoglyceride/cosolvent combinations.

Additionally, U.S. Pat. No. 5,312,122 discloses the use of monoglycerides and fatty acid esters, alone or in combination, as a permeation enhancer mixture for ST 1435, a synthetic progestogen. Specific fatty acid sters or desirable properties are not disclosed.

U.S. Pat. No. 5,026,556 discloses a composition for the transdermal delivery of buprenorphine comprising an amount of buprenorphine in a carrier comprising a polar solvent material selected from the group consisting of $C_3$–$C_4$ diols, $C_3$–$C_6$ triols, and mixtures thereof; and a polar lipid material selected from the group consisting of fatty alcohol esters, fatty acid esters, and mixtures thereof. Ethyl palmitate is disclosed as a suitable polar lipid material.

U.S. Pat. No. 5,352,456 discloses a transdermal device which provides an initial pulse of drug followed by a substantially lower continues rate. The device comprises a drug reservoir comprising the drug dissolved in a carrier and a volatile permeation enhancer. The volatile permeation enhancer is depleted from the reservoir by evaporation through the backing layer causing the decrease in drug delivery rate. The volatile permeation enhancers are described as comprising a vapor pressure of greater than about 10 mm Hg at 25° C.

U.S. Pat. No. 5,149,538 discloses the transdermal delivery of an opioid. Preferred permeation enhancers are saturated and unsaturated fatty alcohols, fatty alcohol esters, or fatty acids having 8–18 carbon atoms.

U.S. Pat. No. 5,650,165 discloses percutaneous absorption preparations comprising an acrylic copolymer, a fatty acid ester comprising a higher fatty acid having 12–16 carbon atoms and a lower monohydric alcohol having 1–4 carbon atoms, and a monoglyceride comprising a higher fatty acid having 8–10 carbon atoms.

U.S. Pat. No. 5,747,069 discloses a percutaneous absorbable preparation containing a drug and an absorption accelerator comprising a monoglyceride and a fatty acid. All of the aforementioned patents are incorporated herein in their entirety by reference.

DESCRIPTION OF TERMS

As used herein, the term "drug" is to be construed in its broadest sense to mean any material which is intended to produce some biological, beneficial, therapeutic, or other intended effect, such as permeation enhancement, for example, on the organism to which it is applied.

As used herein, the term "individual" intends a living mammal and includes, without limitation, humans and other primates, livestock and sports animals such as cattle, pigs and horses, and pets such as cats and dogs.

As used herein, the term "monoglyceride" refers to a monoglyceride or mixture of monoglycerides of $C_{12}$–$C_{20}$ fatty acids and includes, without limitation, glycerol monolaurate (GML), glycerol monooleate (GMO), and glycerol monolinoleate (GMLO).

As used herein, the term "permeation enhancement" intends an increase in the permeability of skin to a drug in the presence of a permeation enhancer as compared to permeability of skin to the drug in the absence of a permeation enhancer.

As used herein, the term "permeation enhancer" intends an agent or a mixture of agents which, alone or in combination, acts to increase the permeability of the skin to a drug.

As used herein, the term "permeation-enhancing" intends an amount or rate of a permeation enhancer which provides permeation enhancement throughout a substantial portion of the administration period.

As used herein, the phrase "predetermined area of skin" intends a defined area of intact unbroken skin or mucosal tissue. That area will usually be in the range of about 5 cm² to about 100 cm².

As used herein, the phrase "sustained time period" intends at least about 12 hours and will typically intend a period in the range of about one to about seven days.

As used herein, the term "therapeutically effective" amount or rate refers to the amount or rate of drug needed to effect the desired therapeutic result.

As used herein, the term "transdermal" refers to the use of skin, mucosa, and/or other body surfaces as a portal for the administration of drugs by topical application of the drug thereto.

SUMMARY OF THE INVENTION

According to the present invention, it has been discovered that the combination of a monoglyceride permeation enhancer and ethyl palmitate as a cosolvent results in a permeation enhancer which provides enhanced transdermal flux for a variety of drugs. The use of ethyl palmitate as a cosolvent for monoglyceride permeation enhancers has been found to unexpectedly result in superior transdermal flux compared to other monoglyceride/cosolvent mixtures such as GML and lauryl acetate. Additionally, ethyl palmitate does not vaporize during process manufacture to the same extent as other cosolvents such as dodecyl acetate, thus is preferred from a manufacturing standpoint.

The invention provides novel compositions for use with transdermal drug delivery devices and methods for effectively administering drugs and greatly increasing the drug permeability through the skin while reducing the lag time between application of the drug to the skin and attainment of the desired therapeutic effect.

Accordingly, the present invention provides compositions and devices for transdermal administration of at least one drug to the systemic circulation of a patient, at a therapeutically effective rate, by permeation through a body surface or membrane, comprising at least one drug and a permeation-enhancing amount of a permeation enhancer comprising a monoglyceride in combination with ethyl palmitate as a cosolvent. The invention further provides a method for the transdermal coadministration of a drug at a therapeutically effective rate together with a skin permeation-enhancing amount of the monoglyceride/ethyl palmitate permeation enhancer.

While it is known in the art to combine permeation enhancers, this invention utilizes a novel combination of a monoglyceride and ethyl palmitate. Preferred monoglycerides include glycerol monolaurate (GML), glycerol monooleate (GMO), and glycerol monolinoleate (GMLO). Glycerol monolaurate is a particularly preferred monoglyceride.

Therefore, it is an aspect of the present invention is to provide improved drug delivery by means of transdermal systems and compositions.

It is accordingly an aspect of this invention to provide a permeation enhancer composition for use in transdermal compositions, methods, and devices which provides for the transdermal coadministration of a drug at a therapeutically effective rate with improved in vivo efficacy.

It is another aspect of this invention to provide a permeation enhancer composition for use in transdermal compositions, methods, and devices comprising a monoglyceride and a cosolvent wherein the cosolvent is stable and obtainable at a high degree of purity, thus resulting in systems which are more readily characterized.

A further aspect is to increase the transport of drugs across the skin following application of a transdermal therapeutic system.

Another aspect is to eliminate the lag time between the application of a transdermal therapeutic system and attainment of the desired therapeutic flux level.

Another aspect is to improve ease of manufacture of transdermal systems and compositions comprising permeation enhancers.

It is yet another aspect of this invention to provide a permeation enhancer composition for use in transdermal compositions, methods, and devices which provides consistent results from one lot of formulations to another.

Therefore, the invention comprises the following aspects, either alone or in combination:

A composition of matter for transdermally delivering at least one drug at a therapeutically effective rate by permeation through a body surface or membrane comprising, in combination:

(a) at least one drug; and (b) a permeation-enhancing amount of a permeation enhancer comprising a monoglyceride and ethyl palmitate, wherein the drug and permeation enhancer are dispersed within a carrier.

A device for the transdermal administration of at least one drug at a therapeutically effective rate by permeation through a body surface or membrane, comprising:

a) a drug reservoir comprising at least one drug and a permeation-enhancing amount of a permeation enhancer comprising a monoglyceride and ethyl palmitate;

b) a backing on or adjacent the skin distal surface of the drug reservoir;

c) means for maintaining the reservoir in drug- and permeation enhancer-transmitting relation with the body surface or membrane.

The compositions and devices according to this invention preferably comprise a drug selected from the group consisting of anxiolytics, anticholinergics, analgesics, and antispasmodics such as testosterone, estradiol, progesterone, fentanyl, oxybutynin, and buspirone; a monoglyceride selected from the group consisting of glycerol monooleate, glycerol monolinoleate, and glycerol monolaurate. Additionally, the means for maintaining the reservoir in drug- and permeation enhancer-transmitting relation with the body surface or membrane comprises an in-line adhesive or the drug reservoir comprises a pressure sensitive adhesive which also provides said means for maintaining the reservoir in drug- and permeation enhancer-transmitting relation with the body surface or membrane. The devices and compositions may also comprise about 1–15% by weight of a water absorbing polymer such as polyvinyl pyrrolidone and polyvinyl alcohol. Other suitable water soluble and water absorbing polymers are known in the art, such as those disclosed in U.S. Pat. No. 5,176,916, hereby incorporated in its entirety by reference.

Additionally, the invention is directed to a method for the transdermal administration of at least one drug at a therapeutically effective rate comprising simultaneously coadministering to a body surface or membrane a drug and a permeation enhancing amount of a permeation enhancer comprising a monoglyceride and ethyl palmitate.

These and other aspects and advantages of this invention will be readily apparent from the following description with reference to the accompanying figures.

MODES FOR CARRYING OUT THE INVENTION

Figure 1:
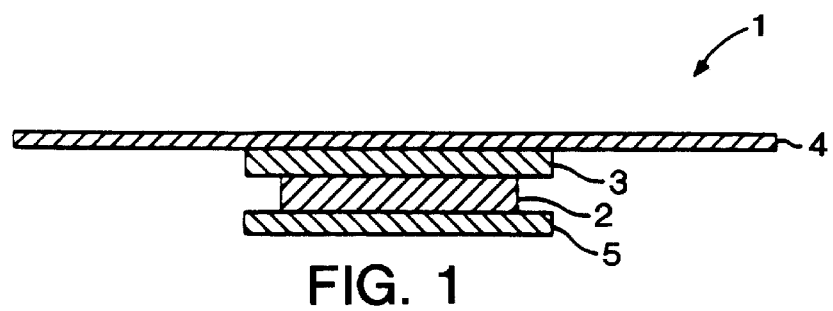
FIG. 1 is a cross-sectional view of one embodiment of a transdermal therapeutic drug delivery device which may be used in accordance with the present invention.

According to the invention, it has been found that a combination of a monoglyceride and ethyl palmitate can be used to effectively enhance the permeability of drugs through body surfaces and particularly through the skin. Specifically, it has been found that monoglycerides and ethyl palmitate enhance the permeability of the skin such that therapeutically effective amounts of a drug can be delivered from reasonably sized devices at therapeutically effective rates. Additionally, ethyl palmitate has a higher molecular weight and lower vapor pressure than prior art monoglyceride cosolvents such as lauryl acetate, thus being superior from a manufacturing standpoint.

The system of the invention is preferably a transdermal drug delivery device comprising a matrix adapted to be placed in drug- and permeation enhancer-transmitting relation with a body surface or membrane such as the skin or mucosa. The system must be of a size useful for the application of the drug and the enhancer to a human body.

The utility of a monoglyceride/ethyl palmitate permeation enhancer has been demonstrated for a variety of different drugs as seen in the Examples that follow. It is believed that this invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, fentanyl, halothane, isoflurane, ketamine hydrochloride, meperidine, methohexital, methoxyflurane, morphine, propofol, sevoflurane, sufentanil, thiamylal, thiopental, aceta.minophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamic acid.

Other representative drugs include benzodiazepines, such as aiprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, cluazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as the esters cf natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

Ethyl palmitate has been demonstrated herein as a suitable cosolvent for GML. Ethyl palmitate may also be used as a cosolvent together with other monoglycerides. Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%.

Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example.

Transdermal drug delivery systems are typically maintained in contact with the skin using an "in-line" contact adhesive, ie, a layer of adhesive positioned between the drug reservoir of the delivery system and the skin. Glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the second permeation enhancer, the glycerol monooleate must have a total monoesters content of at least 65%.

Administration of the drug according to the invention comprises administering the drug at a therapeutically effective rate to an area of a body surface (eg, skin) or membrane and simultaneously administering the monoglyceride and ethyl palmitate to the area of the body surface or membrane at rates which are sufficient to substantially increase the permeability of the area to the drug formulation.

According to the invention, the monoglyceride and ethyl palmitate permeation enhancer and the drug to be delivered are placed in drug- and permeation enhancer-transmitting relationship to the appropriate body surface, preferably in a carrier therefor, and maintained in place for the desired period of time. The drug and permeation enhancer mixture are typically dispersed within a physiologically compatible matrix or carrier which may be applied directly to the body surface or skin as an ointment, gel, cream, suppository or sublingual or buccal tablet, for example, but are more preferably administered from a transdermal therapeutic delivery device as more fully described below. When used in the form of a liquid, ointment, cream, or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of typical compositions as are known to the art.

The monoglyceride/ethyl palmitate permeation enhancer of this invention has a permeation-enhancing effect on the transport of drugs through body surface tissues generally, in addition to the skin. Flowever, because skin is one of the most effective barriers to the permeation of drugs into the body, the effect of a monoglyceride and ethyl palmitate on skin permeation makes it extremely useful in transdermal delivery. The following description of embodiments of the invention is therefore directed primarily to improving systemic delivery of these drugs by permeation through the skin.

Figure 3:
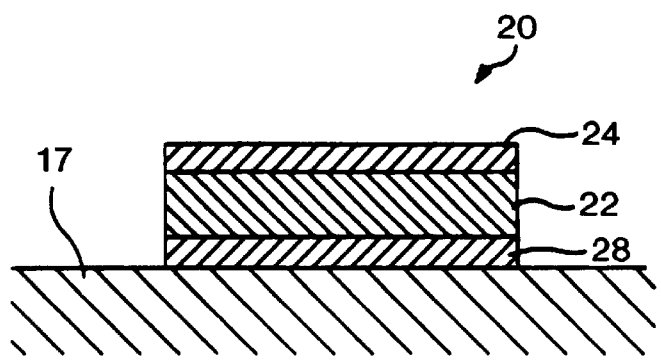
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a drug- and permeation enhancer-containing reservoir ("drug reservoir") 2 which is preferably in the form of a matrix containing the drug and the enhancer dispersed therein. A backing layer 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Backing layer 3 may be permeable or impermeable to the drug and is preferably slightly larger than drug reservoir 2, and in this manner prevents the materials in drug reservoir 2 from adversely interacting with the adhesive in overlay 4. A strippable or removable liner 5 is also provided with device 1 and is removed just prior to application of device 1 to the skin.

Figure 2:
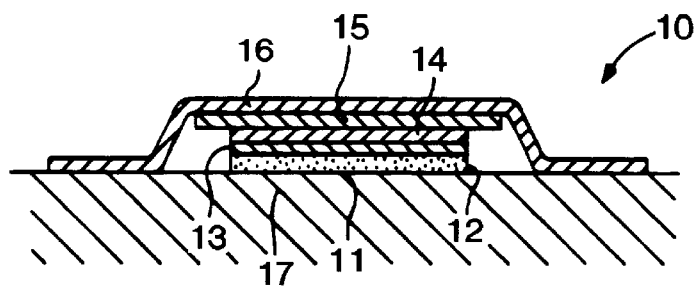
FIG. 2 is a cross-sectional view of another embodiment of a transdermal therapeutic drug delivery device which may be used in accordance with the present invention.

FIG. 2 illustrates another embodiment of the invention, device 10, shown in placement on the skin 17. In this embodiment, the transdermal drug delivery device 10 comprises multi-laminate drug formulation/permeation enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used in zone 12. Zone 14 comprises monoglyceride and ethyl palmitate dispersed throughout and is substantially free of any undissolved drug. A rate-controlling membrane 13 for controlling the release rate of the monoglyceride/ethyl palmitate permeation enhancer from zone 14 to zone 12 is placed between the two zones. A rate-controlling membrane (not shown) for controlling the release rate of the permeation enhancer from zone 12 to the skin may also optionally be utilized and would be present between the skin 17 and zone 12.

The rate-controlling membrane 13 may be fabricated from permeable, semipermeable or microporous materials which are known in the art to control the rate of agents into and out of delivery devices and having a permeability to the permeation enhancer lower than the matrix material of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of a combined drug and enhancer reservoir :such as reservoir 2 in FIG. 1. This reduces the amount of drug in the device while maintaining an adequate supply of permeation enhancer.

Superimposed over the drug formulation/enhancer reservoir 11/12 of device 10 is an impermeable backing 15 and an adhesive overlay 16 as described above with respect to FIG. 1. In addition, a removable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a permeable or microporous skin-contacting membrane, as known to the art from U.S. Pat. No. 4,379,454 (noted above), for example.

An example of a presently preferred transdermal delivery device 20 is illustrated in FIG. 3. Device 20 comprises a drug reservoir 22 containing both the drug and the monoglyceride/ethyl palmitate permeation enhancer. Reservoir 22 is preferably in the form of a matrix containing the drug and the permeation enhancer dispersed therein. Reservoir 22 is sandwiched between a backing layer 24, which is preferably impermeable to both the drug and the permeation enhancer mixture, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the drug or, in particular, the monoglyceride/ethyl palmitate permeation enhancer. The adhesive layer 28 may optionally contain permeation enhancer and/or drug. A removable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-side of the rate-controlling membrane.

Alternatively, reservoir 22 may be in the form of a matrix containing the drug and permeation enhancer dispersed within a suitable adhesive, preferably a pressure sensitive adhesive. Such pressure sensitive adhesives include, but are not limited to, polysiloxanes, polyacrylates, polyurethanes, acrylic adhesives including crosslinked or non-crosslinked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof.

The matrix formulations according to this embodiment comprise the adhesive containing drug and permeation enhancer laminated to a backing on one surface and to a release liner on the other. In addition to the drug and permeation enhancer, the matrix or carrier may also contain dyes, anti-irritants, pigments, inert fillers, excipients and other conventional components of pharmaceutical products or transdermal devices known to the art. For example, the matrix may also be provided with hydrophilic water absorbing polymers known in the art such as polyvinyl alcohol and polyvinyl pyrrolidone individually or in combination and/or an anti-irritant, preferably a corticosteroid such as hydrocortisone.

Various materials suited for the fabrication of the various layers of the transdermal devices of FIGS. 1, 2 or 3 are known in the art or are disclosed in the aforementioned transdermal device patents previously incorporated herein by reference.

The matrix making up the drug/permeation enhancer reservoir can be a gel or a polymer. Suitable materials are compatible with the drug, GML or other monoglyceride, ethyl palmitate, and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to a drug and monoglyceride/ethyl palmitate, which are essential to the invention, the matrix may also contain stabilizers, dyes, permeation enhancers, pigments, inert fillers, anti-irritants, tackifiers, excipients and other conventional components of transdermal delivery devices as are known in the art. For example, the matrix may also be provided with hydrophilic water absorbing polymers known in the art such as polyvinyl alcohol and polyvinyl pyrrolidone individually or in combination.

The amounts of the drug that are present in the therapeutic device, and that are required to achieve a therapeutic effect, depend on many factors, such as the minimum necessary dosage of the particular drug; the permeability of the matrix, of the adhesive layer and of the rate-controlling membrane, if present; and the period of time for which the device will be fixed to the skin. There is, in fact, no upper limit to the maximum amounts of drug present in the device. The minimum amount of each drug is determined by the requirement that sufficient quantities of drug must be present in the device to maintain the desired rate of release over the given period of application.

The drug is generally dispersed through the matrix at a concentration in excess of saturation, i.e. at unit activity. The amount of excess is determined by the intended useful life of the system. However, the drug may be present at initial levels below saturation without departing from this invention. Generally, the drug may be present at initially subsaturated levels when: 1) the skin flux of the drug is sufficiently low such that the reservoir drug depletion is slow and small; 2) non-constant delivery of the drug is desired or acceptable; and/or 3) saturation of the reservoir is achieved in use due to migration of water into the reservoir from the skin, where water is abundantly available.

The monoglyceride and ethyl palmitate permeation enhancer is dispersed throughout the matrix, preferably at a concentration sufficient to provide permeation-enhancing concentrations of permeation enhancer in the reservoir throughout the anticipated administration period.

In the present invention, the drug is delivered through the skin or other body surface at a therapeutically effective rate (that is, a rate that provides an effective therapeutic result) and the monoglyceride/ethyl palmitate permeation enhancer is delivered at a permeation-enhancing rate (that is, a rate that provides increased permeability of the application site to the drug) for a predetermined time period.

A preferred embodiment of the present invention is a multilaminate, such as that illustrated in FIG. 3 (either with or without a rate-controlling membrane) wherein reservoir 22 comprises, by weight, 30–90% polymer (preferably EVA having a vinyl acetate content of 40%), 1–40% drug, 1–50%, more preferably 1–25%, and most preferably 4–15% GML, and 1–40%, more preferably 1–20%, and most preferably 4–12% ethyl palmitate. The in-line adhesive layer 28 comprises an adhesive which is compatible with the permeation enhancer.

Another preferred embodiment of the present invention is a monolith, (not depicted) wherein the drug reservoir comprises, by weight, 30–90%, more preferably, 30–70% of a pressure sensitive adhesive, 1–40% drug, 1–40%, more preferably 1–25%, and most preferably 4–15% GML, and 1–40%, more preferably 1–20%, and most preferably 4–12% ethyl palmitate, and optionally 1–15 wt % of a water absorbing polymer such as polyvinyl pyrroliclone.

The devices of this invention can be designed to effectively deliver a drug for an extended time period of up to 7 days or longer. Seven days is generally the maximum time limit for application of a single device because the skin site is adversely affected by a period of occlusion greater than 7 days. Where it is desired to have drug delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein. The following examples are offered to illustrate the practice of the present invention and are not intended to limit the invention in any manner.

EXAMPLE 1

The effect of various permeation enhancers on the transdermal flux of progesterone was studied. The drug/permeation enhancer reservoirs were prepared by mixing ethylene vinyl acetate having a vinyl acetate content of 40 percent ("EVA 40", USI Chemicals, Illinois) in an internal mixer (Brabender type) until the EVA 40 pellets fused. Progesterone, GMI (Danisco Ingredients) and ethyl palmitate (EP) (CTC Organics, Atlanta, Ga.), were then added as shown in Table 1A. The mixture was blended, cooled, and calendered to a 5 mil thick film.

The film was then laminated to a Cotran® ( 3M, St. Paul, Minn.) backing on one side and an acrylate contact adhesive (3M, St. Paul, Minn.) on the opposite side. The laminate was then cut into 2.54 cm² circles using a steel punch.

Drug in adhesive systems were prepared by adding GML, PVP (XL-10, K29-32 ISP Technologies, Inc, Calvert City, Ky.), and EP to polysiloxane adhesive (Dow Corning, Midland, Mich.) in THF/ethyl acetate solvent at a solvent ratio of approximately 50/50. The solution was mixed for approximately 1 hour at which time the drug (progesterone) is added with additional mixing for approximately 1 hour. The compositions of these systems are also shown in Table 1A. The solution was then cast to 12 mil thickness on a release liner film (3M fluorocoated 1022) and placed in an oven at about 70° C. for approximately 45 minutes, then laminated to a polyethylene backing (Cotran 9220, 3M). The laminate was then cut into 2.54 cm² circles using a steel punch.

TABLE IA

Drug/Permeation Enhancer Reservoir Composition (weight percent)

| FORMULATION | WEIGHT PERCENT |
| --- | --- |
| A. progesterone/EVA 40 | 5/95 |
| B. progesterone/GML/EP/EVA 40 | 5/20/12/63 |
| C. progesterone/polysiloxane | 5/95 |
| D. progesterone/GML/EP/PVP/polysiloxane | 5/3/7/2.5/82.5 |

Circular pieces of human epidermis were mounted on the receptor compartment of horizontal permeation cells with the stratum corneum facing the donor compartment of the cell. The release liner of the laminate was removed and the systems were centered over the stratum corneum side of the epidermis. The donor compartment was then clamped with the receptor compartment. A known volume of receptor solution (1% Tween 20 in water) was equilibrated at 35° C. and placed in the receptor compartment. Air bubbles were removed from the receptor compartment, the cell was capped and placed in a water bath shaker at 35° C.

At given time intervals, the entire receptor solution was removed from the cells and replaced with an equal volume of fresh receptor solutions previously equilibrated at 35° C. The receptor solutions are stored in capped vials at 4° C. until assayed for progesterone content by high performance liquid chromatography (HPLC). The tests were run in triplicate on 2 skin donors.

From the drug concentration and the volume of the receptor solutions, the area of permeation and the time interval, the flux of the drug through the epidermis was calculated as follows: (drug concentration×volume of receptor)/(area×time)=flux ($\mu g/cm^2 \cdot hr$). The average flux ratios of each formulation comprising the permeation enhancer compared to the formulation without permeation enhancers for each of the skins tested is depicted in Table 1B.

TABLE 1B

Average Flux Ratios

| FORMULATION | FLUX RATIO SKIN I (FORM. X/CONTROL) | FLUX RATIO SKIN II (FORM. X/CONTROL) |
| --- | --- | --- |
| A. | 1.00 | 1.00 |
| B. | 5.67 | 6.13 |
| C. | 1.00 | 1.00 |
| D. | 1.70 | 2.09 |

EXAMPLE 2

The effect of various permeation enhancer mixtures on the transdermal flux of buspirone was studied. The drug/permeation enhancer reservoirs were prepared according to the procedure set forth in Example 1. Buspirone, GML, and ethyl palmitate, were added as shown in Table 2A.

TABLE 2A

Drug/Permeation Enhancer Reservoir Composition (weight percent)

| FORMULATION | WEIGHT PERCENT |
| --- | --- |
| E. buspirone/EVA 40 | 20/80 |
| F. buspirone/GML/EVA 40 | 20/20/60 |
| G. buspirone/GML/EP/EVA 40 | 20/20/12/48 |
| H. buspirone/EP/EVA 40 | 20/12/68 |

The skin flux experiments according to Example 1 were conducted using 0.05 M $KH_2PO_4/K_2HPO_4$, pH 6.5, as the receptor solution. The average flux ratios of each formulation comprising the permeation enhancer mixture compared to the formulation without permeation enhancers for each of the skins tested is depicted in Table 2B.

TABLE 2B

Average Flux Ratios

| FORMULATION | FLUX RATIO SKIN I (FORM. X/CONTROL) | FLUX RATIO SKIN II (FORM. X/CONTROL) |
| --- | --- | --- |
| E. | 1.00 | 1.00 |
| F. | 9.19 | 8.16 |
| G. | 10.03 | 8.15 |
| H. | 1.28 | 1.19 |

EXAMPLE 3

The effect of various permeation enhancer mixtures on the transdermal flux of estradiol was studied. The drug/permeation enhancer reservoirs were prepared according to the procedures set forth in Example 1. Estradiol, GML, PVP, and ethyl palmitate, were added as shown in Table 3A.

TABLE 3A

Drug/Permeation Enhancer Reservoir Composition (weight percent)

| FORMULATION | WEIGHT PERCENT |
| --- | --- |
| I. estradiol/EVA 40 | 5/95 |
| J. estradiol/GML/EP/EVA 40 | 5/20/12/63 |
| K. estradiol/polysiloxane | 2/98 |
| L. estradiol/GML/EP/PVP/polysiloxane | 2/3/7/2.5/85.5 |

The skin flux experiments according to Example 1 were conducted using 1% Tween 20 in water as the receptor solution. The average flux ratios of each formulation comprising the permeation enhancer mixture compared to the formulation without permeation enhancers for each of the skins tested is depicted in Table 3B.

TABLE 3B

Average Flux Ratios

| FORMULATION | FLUX RATIO SKIN I (FORM. X/CONTROL) | FLUX RATIO SKIN II (FORM. X/CONTROL) |
|---|---|---|
| I. | 1.00 | 1.00 |
| J. | 2.05 | 2.11 |
| K. | 1.00 | 1.00 |
| L. | 1.31 | 1.38 |

EXAMPLE 4

The effect of GML and ethyl palmitate on the transdermal flux of oxybutynin from drug in adhesive matrix formulations was determined. The systems having the compositions shown in Table 4A, were prepared by the procedure set forth in Example 1.

TABLE 4A

Drug/Permeation Enhancer Reservoir Composition (weight percent)

| DRUG RESERVOIR | WEIGHT PERCENT |
|---|---|
| M. oxybutynin base/polysiloxane | 20/80 |
| N. oxybutynin base/GML/EP/PVP/polysiloxane | 20/3/7/2.5/67.5 |

The skin flux experiments according to Example 1 were conducted using 0.05 M $KH_2PO_4/K_2HPO_4$, pH 6, as the receptor solution. The average flux ratios of each formulation comprising the permeation enhancer mixture compared to the formulation without permeation enhancers for each of the skins tested is depicted in Table 4B.

TABLE 4B

Average Flux Ratios

| FORMULATION | FLUX RATIO SKIN I (FORM. X/CONTROL) | FLUX RATIO SKIN II (FORM. X/CONTROL) |
|---|---|---|
| M. | 1.00 | 1.00 |
| N. | 1.86 | 1.46 |

EXAMPLE 5

The effect of GML and ethyl palmitate on the transdermal flux of buspirone from drug in adhesive matrix formulations was determined. The drug/permeation enhancer reservoirs, having the compositions shown in Table 5A, were prepared by the procedure described in Example 1.

TABLE 5A

Drug/Permeation Enhancer Reservoir Composition (weight percent)

| DRUG RESERVOIR | WEIGHT PERCENT |
|---|---|
| O. buspirone/polysiloxane | 5/95 |
| P. buspirone/GML/EP/PVP/polysiloxane | 5/3/7/2.5/82.5 |

The skin flux experiments according to Example 1 were conducted using 0.05 M $KH_2PO_4/K_2HPO_4$, pH 6.5, as the receptor solution. The average flux ratios of each formulation comprising the permeation enhancer mixture compared to the formulation without permeation enhancers for each of the skins tested is depicted in Table 5B.

TABLE 5B

Average Flux Ratios

| FORMULATION | FLUX RATIO SKIN I (FORM. X/CONTROL) | FLUX RATIO SKIN II (FORM. X/CONTROL) |
|---|---|---|
| O. | 1.00 | 1.00 |
| P. | 3.53 | 3.77 |

EXAMPLE 6

The transdermal flux of testosterone from drug in adhesive matrix formulations comprising GML and either dodecyl acetate (Inoue Perfumery Mfg. Co. LTD, Tokyo, Japan) or ethyl palmitate was determined. The drug/permeation enhancer reservoirs, having the compositions shown in Table 2, were prepared by the procedure described in Example 1.

TABLE 6

Drug/Permeation Enhancer Reservoir Composition (weight percent)

| DRUG RESERVOIR | WEIGHT PERCENT |
|---|---|
| testosterone/EVA 40 | 2/98 |
| testosterone/GML/DA/PVP/polysiloxane | 5/4/7/10/74 |
| testosterone/GML/DA/PVP/polysiloxane | 5/8/7/5/75 |
| testosterone/GML/DA/PVP/polysiloxane | 5/12/7/5/71 |
| testosterone/GML/EP/PVP/polysiloxane | 5/4/7/10/74 |
| testosterone/GML/EP/PVP/polysiloxane | 5/8/7/5/75 |

Figure 4:
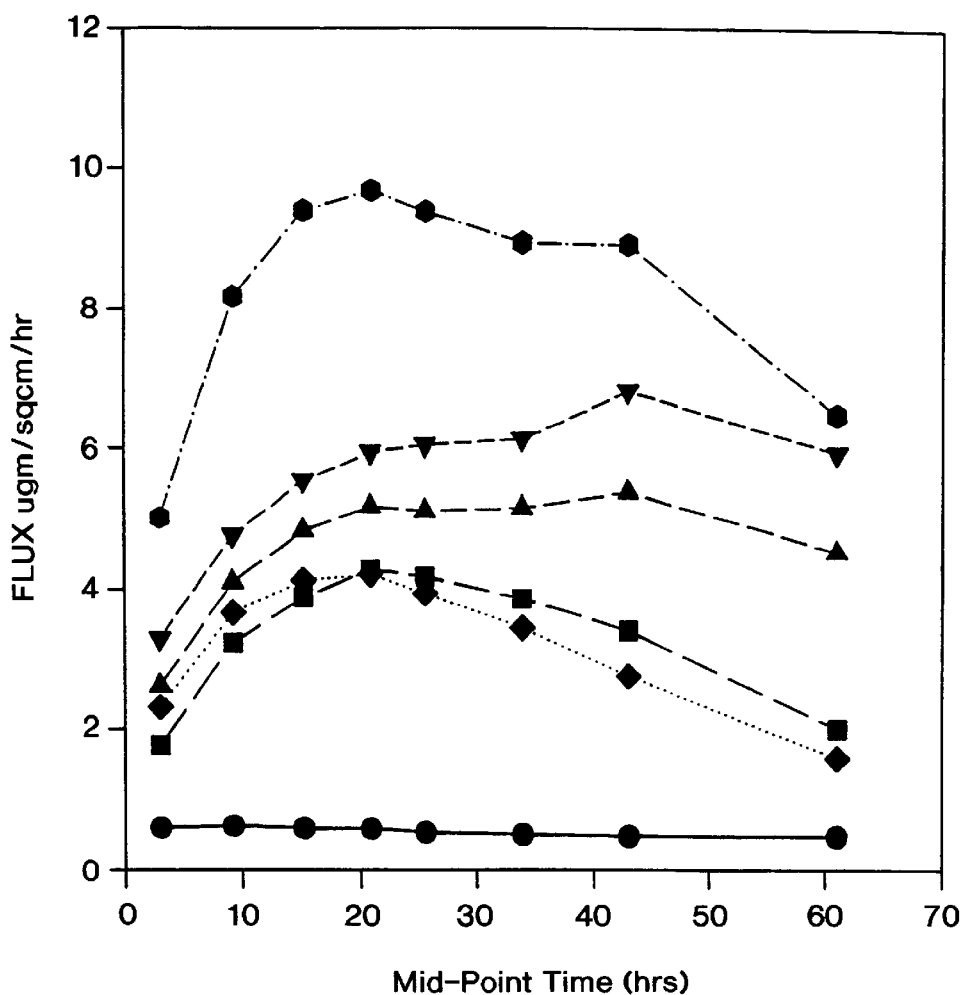
FIG. 4 is a graph of the flux of testosterone through human epidermis at 35° C. from systems using various enhancers.

The skin flux experiments according to Example 1 were conducted using 0.10% phenol/water as the receptor solution. FIG. 4 depicts the results.

The invention has been described in detail with particular reference to certain preferred embodiments thereof, but it will be understood that variations and modifications can be affected within the scope and spirit of the invention.

What is claimed is:

1. A composition of matter for transdermally delivering at least one drug at a therapeutically effective rate by permeation through a body surface or membrane comprising, in combination:

(a) at least one drug; and (b) a permeation-enhancing amount of a permeation enhancer comprising 1–50% by weight of a monoglyceride and 1–50% by weight ethyl palmitate, wherein the drug and permeation enhancer are dispersed within a carrier.

2. A composition according to claim 1 wherein the monoglyceride is selected from glycerol monooleate, glycerol monolinoleate, and glycerol monolaurate.

3. A composition according to claim 1 wherein the drug is present in an amount in excess of its saturation in the carrier.

4. A composition according to claim 1 comprising 1–40% by weight of at least one drug, and 30–90% by weight of a polymeric carrier.

5. A composition according to claim 4 comprising 1–25% by weight glycerol monolaurate and 1–20% by weight ethyl palmitate.

6. A composition according to claim 5 comprising 4–15% by weight glycerol monolaurate and 4–12% by weight ethyl palmitate.

7. A composition according to claim 4 wherein the drug is selected from the group consisting of testosterone, estradiol, progesterone, fentanyl, oxybutynin, and buspirone.

8. A device for the transdermal administration of at least one drug at a therapeutically effective rate by permeation through a body surface or membrane, comprising:
   a) a drug reservoir comprising at least one drug and a permeation-enhancing amount of a permeation enhancer comprising 1–50% by weight of a monoglyceride and 1–50% by weight ethyl palmitate;
   b) a backing on or adjacent the skin distal surface of the drug reservoir;
   c) means for maintaining the reservoir in drug- and permeation enhancer-transmitting relation with the body surface or membrane.

9. A device according to claim 8 wherein the monoglyceride is selected from the group consisting of glycerol monooleate, glycerol monolinoleate, and glycerol monolaurate.

10. A device according to claim 8 wherein the drug is selected from the group consisting of anxiolytics, anticholinergics, analgesics, and anti-spasmodics.

11. A device according to claim 8 wherein the drug is a steroid.

12. A device according to claim 8 wherein the drug is selected from the group consisting of testosterone, estradiol, progesterone, fentanyl, oxybutynin, and buspirone.

13. A device according to claim 8 wherein the means for maintaining the reservoir in drug- and permeation enhancer-transmitting relation with the body surface or membrane is an in-line adhesive.

14. A device according to claim 8 wherein the drug reservoir comprises a pressure sensitive adhesive which also provides said means for maintaining the reservoir in drug- and permeation enhancer-transmitting relation with the body surface or membrane.

15. A device according to claim 14 wherein the pressure sensitive adhesive is selected from the group consisting of polysiloxanes, polyacrylates, polyurethanes, crosslinked or non-crosslinked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof.

16. A device according to claim 8 wherein the drug reservoir comprises:
   I) 1–40% by weight of at least one drug,
   ii) 1–40% by weight ethyl palmitate,
   iii) 1–50% by weight glycerol monolaurate, and
   iv) 30–90% by weight polymeric carrier.

17. A device according to claim 16 comprising 1–25% by weight glycerol monolaurate and 1–20% by weight ethyl palmitate.

18. A device according to claim 17 comprising 4–15% by weight glycerol monolaurate and 4–12% by weight ethyl palmitate.

19. A device according to claim 16 wherein said polymeric carrier comprises ethylene vinyl acetate.

20. A device according to claim 8 wherein the drug reservoir comprises:
   I) 1–40% by weight of a drug,
   ii) 1–40% by weight ethyl palmitate,
   iii) 1–40% by weight glycerol monolaurate, and
   iv) 30–90% by weight pressure sensitive adhesive.

21. A device according to claim 20 comprising 1–25% by weight glycerol monolaurate and 1–20% by weight ethyl palmitate.

22. A device according to claim 21 comprising 4–15% by weight glycerol monolaurate and 4–12% by weight ethyl palmitate.

23. A device according to claim 20 further comprising 1–15% by weight of a water absorbing polymer selected from the group consisting of polyvinyl pyrrolidone and polyvinyl alcohol.

24. A device for the transdermal administration of at least one drug at a therapeutically effective rate by permeation through a body surface or membrane, comprising:
   a) a first reservoir comprising at least one drug and a permeation-enhancing amount of a permeation enhancer comprising a monoglyceride and ethyl palmitate;
   b) a second reservoir comprising an additional amount of the permeation enhancer;
   c) a rate controlling membrane between the first and second reservoirs;
   d) a backing on or adjacent the skin distal surface of the first reservoir; and
   e) means for maintaining the reservoir in drug- and permeation enhancer-transmitting relation with the body surface or membrane.

25. A device according to claim 24 wherein the monoglyceride is selected from glycerol monooleate, glycerol monolinoleate, and glycerol monolaurate.

26. A device according to claim 24 wherein the drug is selected from the group consisting of anxiolytics, anticholinergics, analgesics, and anti-spasmodics.

27. A device according to claim 24 wherein the drug is a steroid.

28. A device according to claim 24 wherein the drug is selected from the group consisting of testosterone, estradiol, progesterone, fentanyl, oxybutynin, and buspirone.

29. A method for the transdermal administration of at least one drug at a therapeutically effective rate comprising simultaneously coadministering to a body surface or membrane a drug and a permeation enhancing amount of a permeation enhancer comprising a monoglyceride and ethyl palmitate.

30. A method according to claim 29 further comprising maintaining said coadministration of drug and permeation enhancer for a period of time sufficient to produce a beneficial effect.

31. A method according to claim 29 wherein the monoglyceride is selected from glycerol monooleate, glycerol monolinoleate, and glycerol monolaurate.

32. A method according to claim 29 wherein the drug is selected from the group consisting of anxiolytics, anticholinergics, analgesics, and anti-spasmodics.

33. A method according to claim 29 wherein the drug is a steroid.

34. A method according to claim 29 wherein the drug is selected from the group consisting of testosterone, estradiol, progesterone, fentanyl, oxybutynin, and buspirone.

35. A composition according to claim 1 wherein the drug is present in a saturation amount in the carrier.

36. A composition according to claim 1 wherein the drug is present in an amount below saturation in the carrier.

* * * * *